United States Patent [19]

Greenleaf et al.

[11] 4,105,018
[45] Aug. 8, 1978

[54] ACOUSTIC EXAMINATION, MATERIAL CHARACTERIZATION AND IMAGING OF THE INTERNAL STRUCTURE OF A BODY BY MEASUREMENT OF THE TIME-OF-FLIGHT OF ACOUSTIC ENERGY THERETHROUGH

[75] Inventors: James F. Greenleaf; Steven A. Johnson, both of Rochester, Minn.

[73] Assignee: University of Utah, Salt Lake City, Utah

[21] Appl. No.: 654,419

[22] Filed: Feb. 2, 1976

[51] Int. Cl.² .................................................. A61B 10/00
[52] U.S. Cl. ......................................... 128/2 V; 73/597; 73/602; 128/2.05 Z
[58] Field of Search .......... 128/2 A, 2 R, 2 V, 2.05 Z, 128/24 A; 310/9.6; 73/67.8 S, 597, 598, 599, 600, 602, 618

[56] References Cited

U.S. PATENT DOCUMENTS

| 3,023,611 | 3/1962  | Howry .................. 128/2 V |
| 3,156,110 | 11/1964 | Clyngs .................. 128/2 V |
| 3,177,382 | 4/1965  | Green .................... 310/9.6 |
| 3,606,879 | 9/1971  | Estes ................. 128/2.05 Z |
| 3,778,756 | 12/1973 | Houston et al. ......... 128/2 V |
| 3,830,223 | 8/1974  | Beretsky ............... 128/2 V |
| 3,878,373 | 4/1975  | Blum ..................... 128/2 A |
| 3,909,771 | 9/1975  | Pickering et al. ........ 73/67.8 S |
| 3,918,024 | 11/1975 | Macovski ............... 73/67.8 S |

OTHER PUBLICATIONS

Greenleaf et al, "Acoustical Holography", vol. 6, Plenum Press, New York/London, 1975, pp. 71–79.
Greenleaf et al, "Acoustical Holography", vol. 5, Plenum Press, New York/London, 1974, pp. 591–603.

*Primary Examiner*—William E. Kamm

[57] ABSTRACT

Pulses of acoustic energy are transmitted from a plurality of different directions through a plane of interest, or a number of adjacent planes of interest, of a body to be examined. The body may be biological or non-biological. Time-of-flight of the pulses is measured for individual paths through the body, and from the data thus obtained the spatial distribution of the acoustic velocity through the plane or planes within the body is reconstructed using a mathematical reconstruction technique. The velocity values thus obtained, which are uniquely determinative of the acoustic index of refraction at each point, have diagnostic value, and they can further be displayed by means of a cathode ray tube or other imaging device to provide an image of the internal structure along each plane. The disclosed technique has the advantage of being highly independent of acoustic attenuation and reflections occurring along the paths.

30 Claims, 9 Drawing Figures

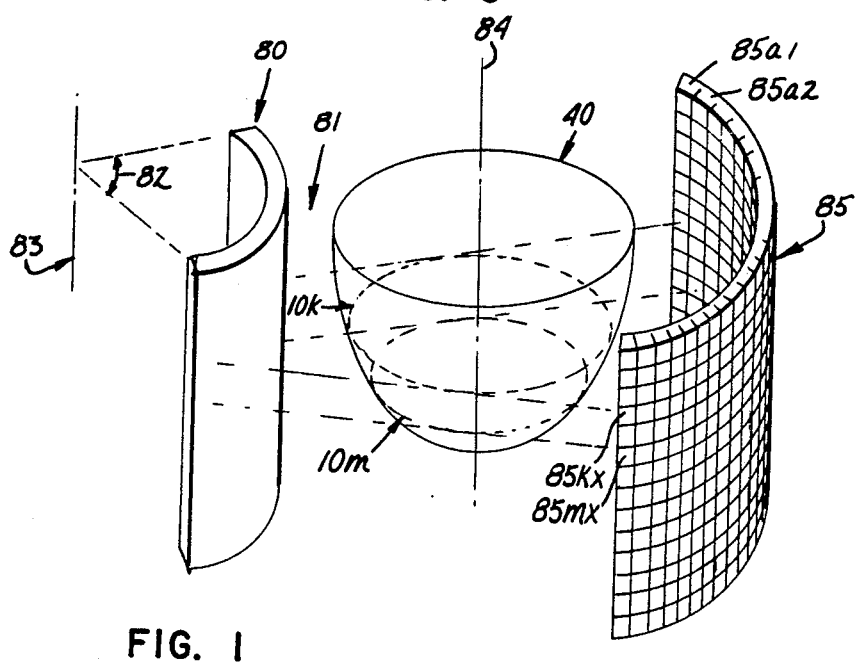
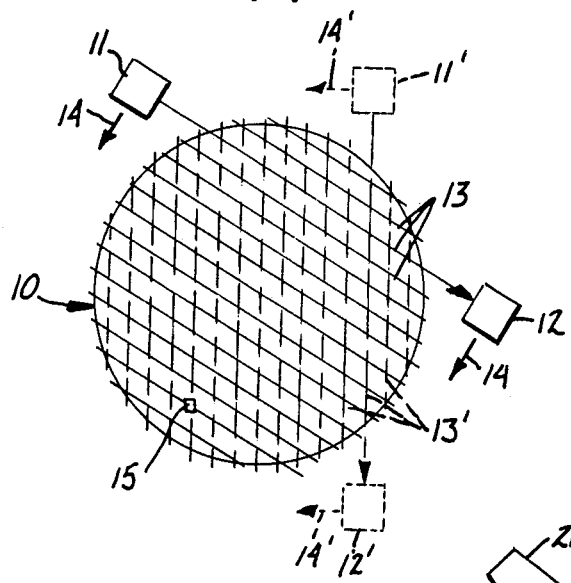
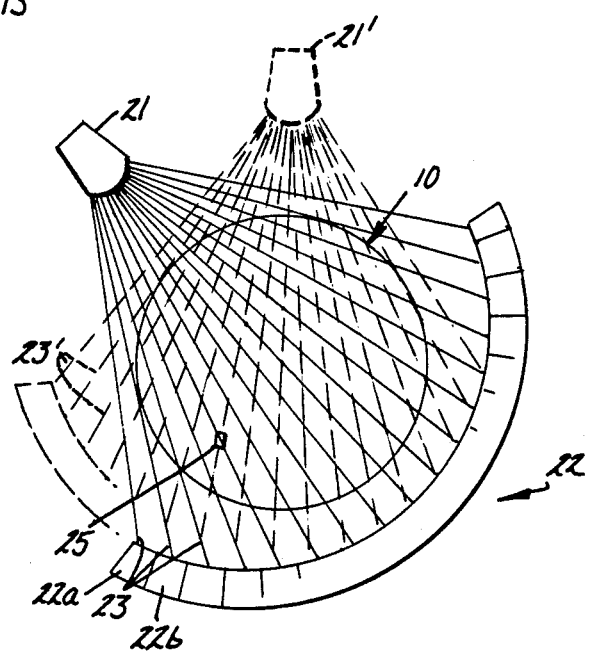

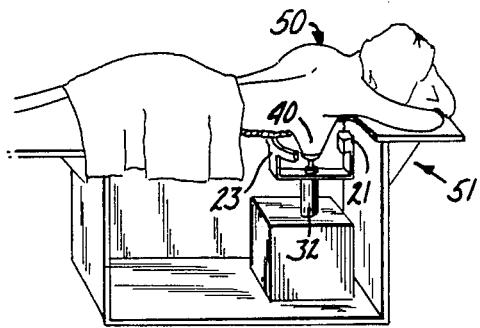
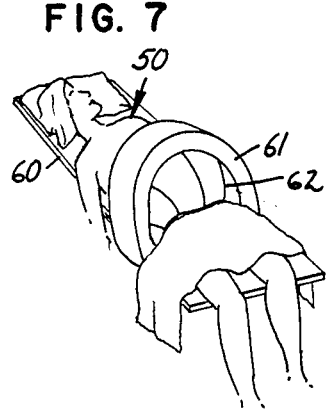
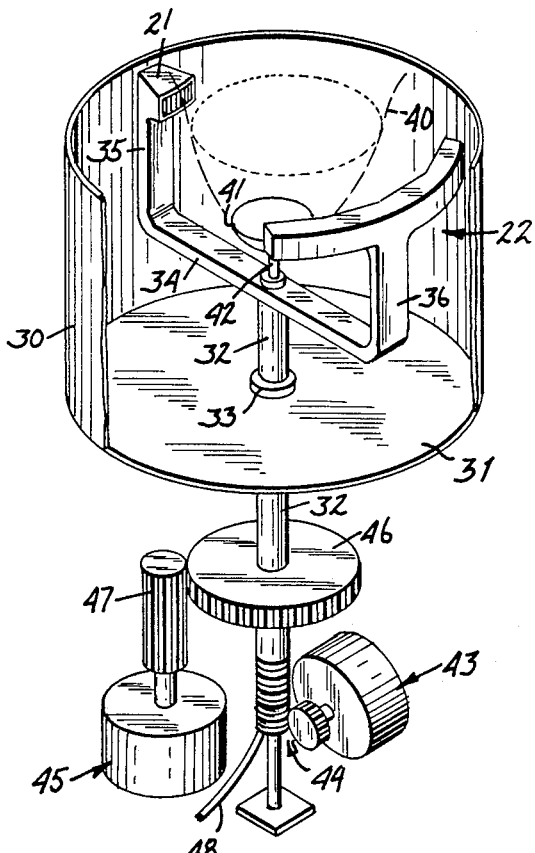
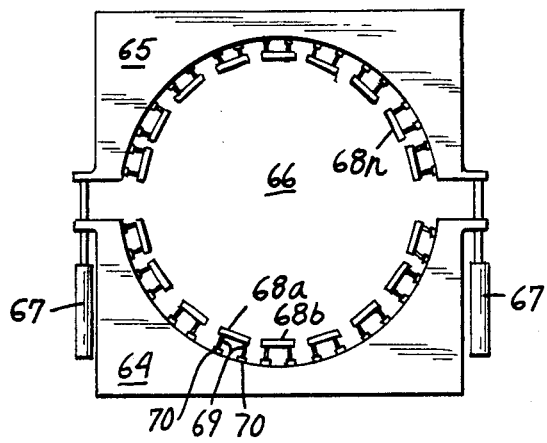
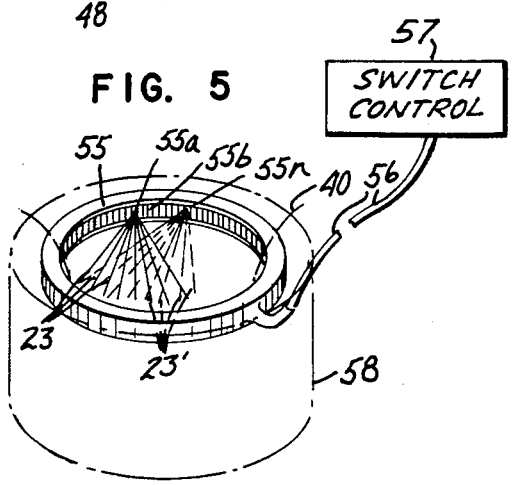

ACOUSTIC EXAMINATION, MATERIAL CHARACTERIZATION AND IMAGING OF THE INTERNAL STRUCTURE OF A BODY BY MEASUREMENT OF THE TIME-OF-FLIGHT OF ACOUSTIC ENERGY THERETHROUGH

BACKGROUND OF THE INVENTION

The invention described herein was made in the course of work under grants HL-04664 and RR-00007 from National Institute of Health, Department of Health, Education and Welfare.

This invention pertains to the field of examination, material characterization and imaging of the internal structure of a body by acoustic techniques. An important application of this field of technology is in diagnostic medicine, wherein safe, accurate and noninvasive examination techniques are becoming increasingly important. X-ray and gamma ray techniques have been used for many years to obtain imagery of the internal structure of the body. Since the dangers of radiation dosage buildup have become better understood, the use of such techniques has been limited to those instances in which the risk represented by the additional X or gamma ray radiation dosage is outweighed by the need for diagnostic information.

However, in other fields which involve examination of areas of the body that are highly susceptible to radiation damage or are statistically prone to form cancers, alternatives to X-ray or gamma ray radiation have been sought. This is particularly true where examination is required on a routine and repeated basis, such as breast examination and in the fields of obstetrics and gynecology.

Promising developments have been made in the field of ultrasonic examination and imaging in order to overcome these problems. Although it is known that very high energy levels of ultrasonic energy are harmful to the human body, low energy levels of exposure are not known to have any harmful effects. Unlike the case with X-ray or gamma ray radiation, there appears to be no reciprocity law (of damage equalizing the product of beam power and exposure time) concerning exposure to ultrasound, so long as the doses are kept below a threshold level. Fortunately, workable signal levels fall well below the danger point. Ultrasonic scanning and imaging devices thus hold the promise of permitting noninvasive examination of internal body structures on a repeated and routine basis, without any presently known, nor suspected, harmful side effects.

Although previously developed ultrasound systems have provided useful information for physicians, they have left considerable room for improvement in terms of resolution, repeatability of measurement, and type and quality of data obtained.

One type of prior art ultrasound device is known as the A-scan which is widely used in various medical fields, including echo cardiography, gynecology and in measuring the position of the brain center line. While not actually providing an image of the tissue, the A-scan provides a display such as a cathode ray tube (CRT) with one axis representing time (depth of penetration), and the other axis showing echoes or return pulses.

Another type of ultrasonic device known as the B-scan is used in obstetrics and cardiology. The B-scan also uses an echo mode, with the transducer scanned laterally along the area of interest of the body. The lateral position of the transducer is displayed on the X-axis, with the depth or distance of the echo being displayed on the Y-axis, and the strength or amplitude of the return echo modulating the brightness of the display. The B-scan is subject to a number of disadvantages resulting from its use of the pulse-echo mode. The echoes or back scatter from some delicate tissue structures may be too weak to be received, particularly since the reflected energy is further attenuated on travelling back through the tissue to the receiver.

Another disadvantage of the B-scan is that the strength of a return from a surface within the body is not only a function of the physical properties of the surface, but also a function of its angular relationship to the pulses. Thus a portion of the surface which happens to be at nearly right angles to the beam gives a strong echo, while another portion of the same surface at a different angle gives a weak return. This same effect makes it difficult or impossible to accurately calibrate B-scan apparatus in order to give consistent and repeatable results, from one clinical setting to another. Slight differences in positioning of the transducer with respect to the patient will give differing brightness levels for the same structures within the body. This lack of consistency is due to the fact that the B-scan does not obtain a quantitative measure of an intrinsic tissue property, but rather measures a property which is an interaction between the measurement system and the body. Recent B-scan methods, known as Compound B-scanning, have employed superimposition of B-scans taken from a number of different angles in an attempt to overcome the above-noted limitations, but such techniques per se still do not measure an intrinsic property of the tissue.

Another prior art acoustic imaging system known as the C-scan involves forming a two dimensional projection for representation of the body at right angles to the beam. In some systems, energy transmitted through the body is received on the other side, and its amplitude serves as a measure of the attenuation in the body. In some recent work, lensing has been employed in an attempt to focus on a single plane within the body, but resolution and contrast are generally poor, and it is not possible to measure an intrinsic property of the tissue at a point in such systems.

In an echo C-scan, range gating is used to select a desired image plane in the body, but the systems are subject to intense specular reflections making it very difficult or impossible to obtain structural data.

Other workers have proposed the use of acoustic holography to produce attenuation-type two dimensional projections of a body similar to the C-scan system. However, the present lack of sensitivity of such systems requires high input acoustic energy levels and therefore raises a possible question of harmful effects. Such systems to date have produced acoustic attenuation C-scan images of the reflection and transmission with their attendant limitations as detailed earlier.

Another acoustic imaging method developed by R. C. Heyser and D. H. LeCroisette is reported in the IEEE 1973 Ultrasonics Symposium Proceedings (IEEE Catolog No. 73CHO 807-8SU). This method involves transmitting swept frequency bursts through a body to a receiver on the opposite side. The received signal is beat against the original signal, giving a frequency difference due to the time delay of propagation. Variations in the difference frequency are then converted to a voltage and painted on a CRT, to give a fringe contour plot which is essentially another form of two dimensional projection.

The above prior art systems, although promising in many respects and very useful in some applications, have not been able to provide quantitative data of intrinsic properties of the internal structure of a body, nor have they been able to provide maps or images along sections passing through the body. This latter type of data and imagery are obtainable in the X-ray field by means of computerized tomography, tomographic reconstruction, etc. and systems commonly called scanners. Unfortunately, however, earlier attempts to apply the same techniques using ultrasonic energy have produced poor results.

In the case of X-ray scanners, the body is exposed to a plurality of beams of radiation through a number of different directions in a plane through which the section is to be imaged, and the amplitude of the received radiation is measured. With enough sets of data to define a matrix of small picture elements in the body, algebraic reconstruction techinques are used to solve for the attenuation coefficient of each picture element. These data can then be displayed graphically by means of a CRT.

We have previously proposed a system which uses an analogous method, with a source of ultrasonic pulses and a receiver or an array of receivers on the other side of the body for receiving beams of ultrasonic energy transmitted through the body. See J. F. Greenleaf, S. A. Johnson et. al., *Acoustic Holography*, Vol. 5, Plenum Press, New York, 1974, pp. 591–603. In that system the amplitude of the received pulses are measured, and an algebraic reconstruction technique is employed to calculate the attenuation coefficient of the various picture elements. The resolution and accuracy of such systems are limited by refraction of the beams within different tissue structures, and to a greater degree by reflection of energy both at the surface of the body and from tissue structure within the body. Since the amount of reflection loss from a given beam is unknown and unpredictable, there is no practical way to discriminate between the amplitude loss in a received signal due to attenuation losses within the body, and the losses due to reflection within the body. This imposes a fundamental limitation upon the resolution of the system, and upon the accuracy of the attenuation coefficient being calculated.

We have discovered that these limitations of acoustic reconstruction measurement and imagery can be avoided by measuring the time-of-flight of acoustic energy pulses through the body, rather than measuring amplitude losses. Mathematical reconstruction techniques are then employed to calculate the spatial distribution of acoustic velocities throughout the plane of measurement in the body. Since only the time of arrival of a beam is detected, and not its amplitude, the system is immune to reflection problems.

The velocity data represents actual measurement of intrinsic properties of the tissue being scanned, and has diagnostic value because different types of tissue, both normal and abnormal, have characteristic acoustic propagation velocities or velocity ranges. Further, the data can be displayed by means of a CRT to give an image or map of values along the section.

The velocity values thus obtained can be used in conjunction with attenuation values to achieve a synergestic effect. The combination of attenuation coefficient data and acoustic velocity data (or index of refraction data) for each picture element in the section gives the diagnostician far greater information than from the sets of data individually.

The index of refraction data obtained on a first calculation can then be used to recalculate the velocity data, or attenuation data, to take into account the bending of ray paths through the body due to the changes in index or refraction from point to point, so as to achieve a higher degree of resolution.

SUMMARY OF THE INVENTION

The present invention provides a method of, and apparatus for, examining the internal structure of a body and characterizing the material therein. Acoustic energy is transmitted through the body from a plurality of different directions, and the time-of-flight of the acoustic energy through the body is measured. The acoustic velocities at a plurality of points within the body are then mathematically reconstructed from the time-of-flight data. The acoustic velocity, which is uniquely determinative of the refractive index, gives quantitative information of an intrinsic property of the material at each point within the body.

The data thus obtained can be visually displayed, as on a cathode ray tube display or the like, to form a map or image as a sectional view through the body along a plane of measurement.

Successive applications of the method for different frequencies of acoustic energy may be obtained, and displayed by different colors on a color CRT display.

Measurement of the amplitude of the acoustic energy transmitted through the body can be made along with the time-of-flight measurements, and a separate reconstruction can be used to calculate attenuation coefficient data at each point within the body, for a plurality of frequencies. The velocity data and the attenuation coefficient data can be correlated against known values as a tool in identifying the material making up the body at each point for which values are obtained.

The velocity data and the attenuation data can be jointly displayed, for a fixed frequency or a plurality of frequencies, by means of a color CRT display, to give a more meaningful map or image of the internal structure of the body.

The index of refraction data can be used on succeeding reconstructions to recalculate velocity and/or attenuation data to obtain higher accuracy and resolution.

BRIEF DESCRIPTION OF THE DRAWING

FIG. 1 is a diagrammatic view illustrating a method which can be used to scan a body according to the present invention;

FIG. 2 is a diagrammatic view of an alternate scanning method which may be used according to the present invention;

FIG. 3 is a view in perspective illustrating the use of a breast scanner according to the present invention, with portions thereof broken away for clarity;

FIG. 4 is an enlarged perspective view, with portions broken away for clarity of a breast scanner according to the present invention;

FIG. 5 is a view in perspective of an alternate embodiment of a breast scanner according to the present invention;

FIG. 6 is a diagrammatic view of an alternate breast scanner according to the present invention employing cylindrical wave fronts;

FIG. 7 is a view in perspective of the manner of use of a body scanning apparatus according to the present invention;

FIG. 8 is a diagrammatic view in elevation of an alternate embodiment of a body scanner according to the present invention.

DESCRIPTION OF THE PREFERRED EMBODIMENTS

Figure 9:
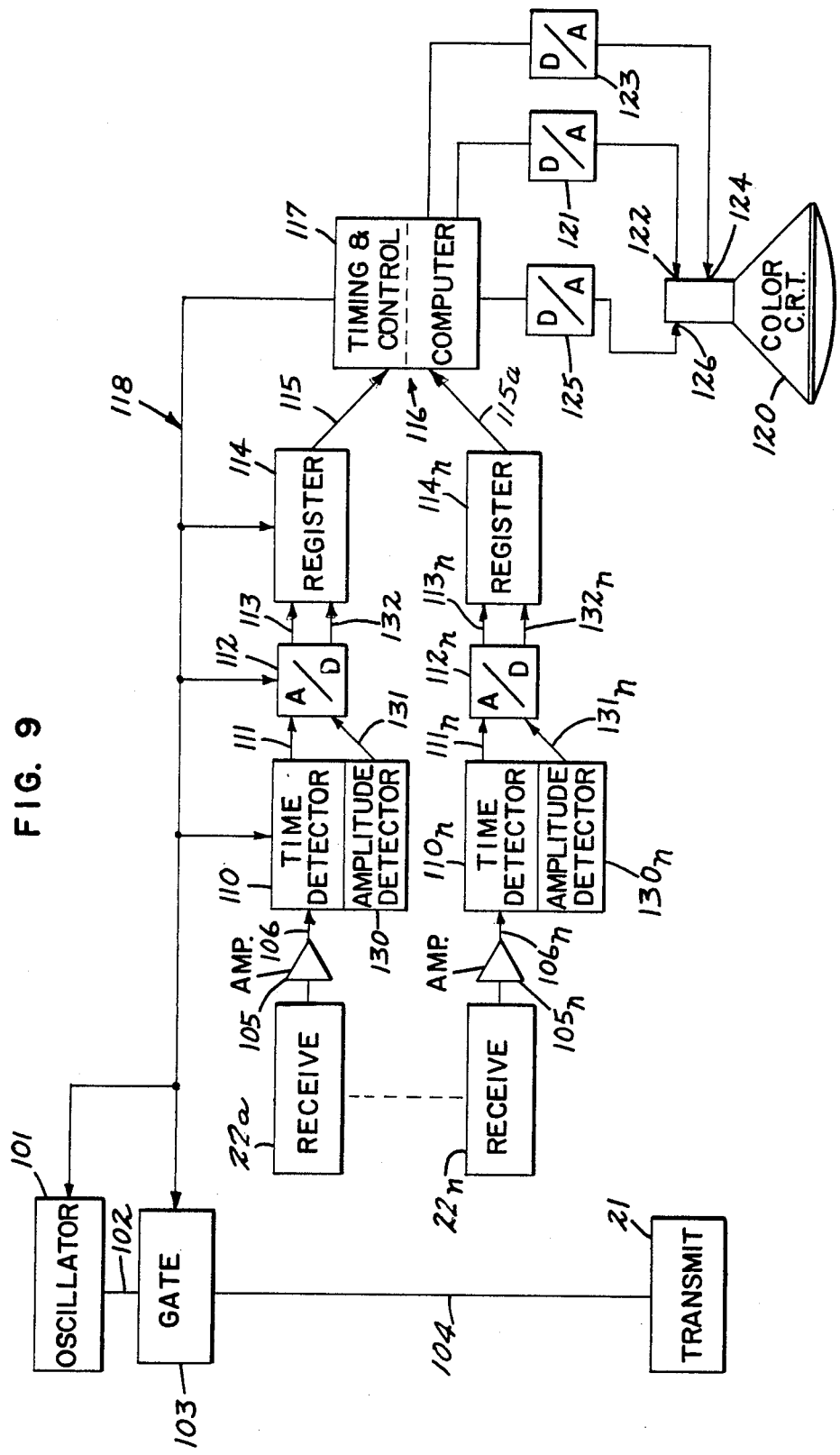
FIG. 9 is a block diagram of an electrical circuit for use in the present invention.

Some basic principles involved in the present invention are diagrammatically illustrated in FIGS. 1 and 2. In FIG. 1, reference numeral 10 represents the outer periphery of a three dimensional body, seen in cross section. A source of acoustic radiation 11 is provided on one side of the body, and a radiation receiver 12 is provided on the other side of the body. Both source 11 and receiver 12 lie in the plane through which body 10 has been sectioned in the view of FIG. 1. A scan is made by transmitting radiation along a plurality of paths 13, with source 11 and receiver 12 being simultaneously scanned along the body as indicated by arrows 14. The received radiation is used to measure time-of-flight through the body as explained more fully hereinafter, and the data is stored for computation later. After completing one scan, either the body is rotated through a small angle, or else the source and receiver are rotated with respect to the body, to a new position indicated by broken lines and primed reference numbers. From the new position, radiation from source 11' traces out a plurality of paths 13' through the body to be received by receiver 12', while the source and receiver scan along the body as indicated by arrows 14'.

Once the ultrasonic scanning and time-of-flight measurements have been made according to the present invention, mathematical reconstruction techniques as are generally known in the prior art are employed for calculating the velocity values at each point. The general theory of mathematical reconstruction is well developed in the prior technical literature, for example, see R. Gordon and G. T. Herman, "Three-Dimensional Reconstruction From Projections: A Review of Algorithms", *International Review of Cytology*, 38:111–151, 1974.

Briefly, it is known that three dimensional functions can be determined from their two dimensional projections obtained by line integrals along paths to the three dimensional function. This mathematical process is known as reconstruction. The line integrals themselves are obtained by transmission of radiation through the three dimensional body along the plane of interest, and receiving it on the other side. A matrix of boundaries defining individual picture elements may be mathematically established throughout the cross section. In FIG. 1, an individual representative picture element 15 is shown. The resolution of the system is established in part by the size and number of the picture elements, which in turn determines the number and spacing of adjacent beam paths 13. Each individual path represents a line integral of the value to be measured. Any given picture element 15 is included in a plurality of such line integrals, and if a sufficient number of sets of data are taken, the resulting set of equations can be solved by known mathematical techniques in conjunction with electronic data processing systems. In the case of X-ray type scanners, and acoustic attenuation type scanners, the value to be solved for at each picture element 15 is the absorption coefficient or attenuation coefficient. In the present invention, the value to be solved for at each picture element 15 is the acoustic velocity at that point, derived from time of flight data for each path 13, 13'.

In FIG. 2, an alternative scanning geometry is shown. Instead of a pencil beam of radiation as shown in FIG. 1, source 21 in FIG. 2 is configured to produce a fan-shaped beam comprising individual rays 23. Receiver 22, positioned on the opposite side of body 10 from source 21, comprises an array of individual sensors 22a, 22b, etc. After a set of data has been taken and stored, the source and receivers are moved to a new position, either by rotation of the body of the sensing apparatus. In the new position, sensor 21' projects rays 23' through the body at a new angle to the receiver now positioned at 22'. A given picture element 25 is intersected by a plurality of individual rays 23, 23', etc., and the resulting line integral equations can be solved for the value at each picture element. Different equations are involved to describe the fan-shaped geometry of the beam rather than the parallel geometry of FIG. 1, but the solution to this problem is known in the literature. Many alternative scanning patterns can be provided in addition to those shown in FIGS. 1 and 2, with the choice being made largely on the basis of simplification of hardware design, and accessibility requirements for various intended areas of the body.

The method and apparatus of the present invention can be used for material characterization and imaging of the internal structure of any type of body through which acoustic energy can be propogated. It thus is applicable to inanimate objects, as well as to biological including human bodies or parts thereof. For example, the present invention may be useful in various industries wherein non-destructive testing techniques are required to ascertain information on the internal structure of an object or product. As previously mentioned, the most important area of applicability of the present invention that is presently contemplated is the field of diagnostic medicine. Accordingly, the embodiments of the present invention described in detail hereinafter are described in terms of medical examination and imaging of the human body, but it will be understood that the same apparatus and methods, with suitable minor modifications, can be adapted for performing the same functions in other fields.

In the field of human medicine, an important application of the present invention is in breast scanning. Apparatus for performing such scans is illustrated in FIGS. 3, 4, 5 and 6. The breast scanner of FIG. 4 includes a basin or water container having a side wall 30 and a bottom 31. A shaft 32 extends upward through the floor 31 of the basin, and suitable sealing means, indicated by reference numeral 33 is provided for preventing water from leaking out. A generally U-shaped transducer mounting bracket has a horizontal portion 34 attached generally perpendicularly to shaft 32, and a pair of upright portions 35 and 36. Ultrasonic source transducer 21 is positioned at the top of upright 35, and a curved array 22 of ultrasonic receiving transducers is similarly positioned atop upright 36. Array 22 includes a great number of individual transducers (not shown in FIG. 4) as schematically indicated in the diagram of FIG. 2, with the number and spacing of individual sensors being chosen according to the picture element resolution of the system. Source 21 of course is adapted for transmitting a fan-shaped beam of ultrasonic energy, and the angular spread of the beam and the corresponding angular extent of array 22 is selected to fully cover the width of a breast to be scanned, which is positioned between source 21 and array 22 as indicated by broken line 40.

A stabilizing cup 41 may be provided beneath the breast to help stabilize and support the breast in position for making a scan. Since several minutes time may be required to make a complete scan, stabilizing cup 41 may help to prevent relative motion which would of course blur the final image. If necessary, a small suction or adhesive device could be incorporated into cup 41 to counteract unwanted buoyancy tendencies in particular cases. Cup 41 is positioned on a stationary shaft 42 which is coaxial with shaft 32. Means may be provided for vertical adjustment of the position of stabilizing cup 41 to accommodate different cases.

The lowermost extension of shaft 32 which extends beneath the water basin is adapted for angular and elevational adjustment as required for making a scan. An elevational adjustment device indicated by reference numeral 43 operatively engages shaft 32 by means of any suitable mechanical linkage, such as cylindrical rack and pinion drive 44, to adjust the elevational position of source 21 and sensor array 22 according to the desired plane of interest through the breast. Although the drawing in FIG. 4 suggests the use of a motor driven rack and pinion arrangement, it will be appreciated that this is only for illustrative purposes, and in fact any suitable hydraulic, mechanical or electromagnetic means could be used to accomplish the necessary vertical adjustment. Similarly, angular adjustment of shaft 32 is provided by means of an angular adjustment device 45 which is operatively connected to shaft 32 by means of a suitable linkage such as gear 46 attached to shaft 32, and gear 47 which is attached to device 45 and is elongated to accommodate varying elevational adjustments of the sensors. Again, although a motor and gear arrangement is suggested in FIG. 4, any means could be provided for angular positioning of shaft 32 and source 21 and sensor array 22.

Electrical connections for ultrasonic source 21 and the sensors of array 22 may be provided by means of internal wiring in the U-shaped transducer mount and shaft 32, and a cable 48. Alternatively, a cable may run from the array 22 and/or transducer 21, to be loosely coiled within the basin and pass through a sealed opening in the wall. It is understood that some portion of the electronic support hardware such as preamplifier or switching networks may be placed within array 22 in close proximity to the receiving transducers.

The manner of use of the scanning apparatus of FIG. 4 will be understood with reference to FIG. 3. In FIG. 3, a patient 50 is positioned horizontally on the surface of a table or bench 51. The surface table 51 has a portion cut away to allow the breast 40 to be suspended in the water inside the basin of the scanning apparatus between source 21 and sensor array 22. The water, or saline solution, provides good ultrasonic contact between the transducers and the skin. In FIG. 4, a portion of the table surface and the basin of the scanning apparatus are deleted for purposes of clarity. The patient thus positioned over the scanning apparatus can lie stationary for the few minutes or less required for a scan. Stabilizing cup 41 is first positioned as required, then the transducer mounting bracket is elevationally positioned so that the plane defined by source 21 and sensor array 22 intersects the breast in a section 10 as required for diagnostic purposes. Source 21 is then energized and measurements made by array 22 are recorded, for successive angular increments around the breast until sufficient data has been obtained. If it is then desired to take an additional section in another plane, the transducer mounting bracket can be vertically repositioned to the new plane of interest.

An alternate implementation of the invention makes use of the desirable properties of cylindrical waves and cylindrical symmetry in the scanning or imaging device. Cylindrical waves may be used to advantage in imaging nearly any object as will be shown below but for purposes of illustration their use is illustrated in the design of a breast scanner shown in FIG. 6.

FIG. 6 illustrates how use of cylindrical symmetry provides added flexibility and speed to the design of a breast scanner. The need to translate the transmitter and receiver transducers is eliminated or minimized by the use of a two-dimensional cylindrical non-closed surface for the transmitter and receiver.

Cylindrical waves are generated by the transmitting transducer 80 and pass into a coupling fluid 81 such as water (or water with additives to better match impedance or index of refraction of the object studied). Transducer 80 is a non-closed circular cylindrical surface which defines an arc of a circle of angle denoted by 82. Angle 82 is sufficiently large to produce a near perfect cylindrical wave at the receiver transducer 85 when no object is present in the coupling fluid 81. Transducers 80 and 85 have surfaces which are coaxial and their common axis of cylindrical symmetry 83 acts as a virtual line of acoustic energy.

Transducers 80 and 85 are fixed relative to each other and can be made to revolve around a common axis of rotation 84 which is located approximately in the center of the object 40 to be reconstructed and studied.

Transducer 85 is composed of a multiplicity of individual receiving transducer elements $85_{a1}$, $85_{a2}$, etc. These transducer elements (such as $85_{a1}$) are connected to a switching network in a manner similar to that shown in FIG. 5. Provisions are made for parallel or serial output or a combination of serial and parallel output from transducer 85 to a time-of-flight detector or other detection devices.

The multiplicity of rows of elements in the array of elements comprising transducer 85 provide for data collection to reconstruct the three-dimension object with only one complete rotation of transducers 80 and 85. Each row of elements, contained in a plane perpendicular to the rotation axis 84, provides data to reconstruct that plane; for example the elements $85_{k1}$, $85_{k2}$, . . . $85_{kx}$ in row defines a plane which intersects the object in plane surface 10k. In a like manner, plane surface 10m is defined by elements $85_{m1}$, . . . $85_{mx}$. In the figure $yx$ ($y$ times $x$) elements are shown as arranged in $x$ columns and $y$ rows.

The advantage of cylindrical and circular cylindrical symmetry in ultrasound image formation is related to the basic property of all cylindrical surfaces; namely, that there is a translation or cylindrical axis. This means that if a cylindrical wave is generated it remains a cylindrical wave in a medium of constant index of refraction. In objects with non-circular cylindrical index of refraction variation, where the direction of cylindrical axis is parallel to the cylindrical axis of the transducer, the waves retain cylindrical symmetry although not necessarily circular cylindrical symmetry. This is equivalent to saying that in cylindrical symmetry each ray is contained in one and only one plane. Even when small (say 10 percent) changes in index of refraction occur which do *not* have cylindrical symmetry the deviations of the rays from such a plane is small. Thus when using cylindrical waves the coupling of information between adjacent planes perpendicular to the cylinder axis is minimal or small compared to the coupling occurring with spherical waves. This is a great advantage and saves computer time since several small multi-plane problems are much easier to solve in total than one large multiple plane problem. Proper use of circular cylindrical symmetry in transmitter and detector symmetry minimizes phase variation across the detector and thus minimizes the requirements for detector resolution. Present X-ray systems *cannot* produce cylindrical symmetric radiation since they do not use coherent sources.

FIG. 5 illustrates an alternate embodiment of a breast scanning device according to the present invention, which employs a completely enclosed 360° array of transducers. Since piezoelectric transducers for use in ultrasonic work can function as either a transmitter or receiver, electronic switching can be employed to take advantage of this fact. In FIG. 5, a ring array 55 has a plurality of individual ultrasonic transducers 55a, 55b, etc., with their size and spacing being determined by resolution requirements. Switching means are provided for the individual transducers and are preferably mounted in ring 55 closely adjacent the transducers. The switching means are connected by means of a cable 56 to a switching control network 57, which may be part of the computer system which supervises measurements and calculates values. In use, ring 55 is immersed in a water or saline container as indicated by broken lines 58, and the patient is again positioned so that the breast 40 being examined passes through the center aperture of ring 55. With ring 55 vertically positioned to the desired plane of interest, scanning is performed as follows.

Switching control network 57 switches a first transducer, for example 55a, to a transmit mode, and all or part of the remaining transducers, including those on the opposite side of the breast from the transmitting transducer, to the received mode. A fan-shaped beam of rays 23 is propogated through the plane of interest, received, and measured. This can be done on a simultaneous basis, or on a sequential basis with individual transducers "listening" one at a time, or in groups, as largely determined by number of and the data rate handling capabilities of the electronic measurement and recording circuits. The switch control 57 then switches another transducer, for example 55n, to the transmit mode and another fan-shaped beam including rays 23' are transmitted through the plane of interest. The number and spacing selected between transducers for transmission is based upon the number of scan points and amount of data required to satisfy the equations.

FIG. 7 illustrates another type of apparatus which may be used according to the present invention, for making scans in the abdominal region. In FIG. 7, the patient 50 is shown horizontally positioned upon a table or work surface 60, with the body passing through an annular member 61. This member includes a plurality of transducers on its inner surface, similar to the device of FIG. 5. Housing 61 is made large enough to permit ingress and egress of the patient and a water bag or plurality of water bags 62 are provided for acoustic coupling between the transducers and the skin. The water bags are filled with water after the patient is in place, and they conform to the shape of the body to provide good acoustic coupling.

An alternate embodiment which does not require water bags is indicated in cross sectional view in FIG. 8. A lower block 64 and an upper block 65 have semicircular cutouts which together define an annular opening 66, through which the patient is positioned with the longitudinal axis of the body normal to the plane of FIG. 8. A pair of actuating devices 67 on either side of the blocks may be used to lift upper block 65 to the position indicated in FIG. 8, to facilitate ingress and egress of the patient. Once the patient is in place, block 65 is lowered onto block 64. A plurality of positionable transducer arrays 68a, b..., etc. are provided on both the upper and lower blocks. These transducer arrays each contain a number of individual ultrasonic transducers. The arrays are mounted to the upper and lower blocks by means of positioning elements 69. A locking device 70 is provided for each positioning element 69. After the patient is in place, supported generally on a horizontal table as in FIG. 7, the individual arrays 68a, 68b, etc. are moved generally inward to contact with the patient's skin to insure good ultrasonic contact. The plurality of locking devices 70 are then locked to hold the arrays in place. Scanning can then take place as described previously with reference to the embodiment of FIG. 5.

Since the sensor arrays are not in a circular configuration at the time a measurement is made, it is necessary to introduce corrections into the reconstruction in order to take this factor into account. At the end of a scan, block 65 is raised to allow egress of the patient, but the arrays are left at their last position. A water bag having cross sectional dimensions roughly the same as a human body is in position in the opening 66, and upper block 65 is lowered, bringing all sensors into contact with the water bag. A second scan is then run to calibrate the system. Since the water in the bag is hemogeneous, the time-of-flight data is indicative of the deviation of the sensor arrays from a perfect circle, and these deviation values can then be used to correct for transducer positioning in the reconstruction of the scan on the patient.

Suitable circuitry for the present invention is indicated in block diagram form in FIG. 9, in which reference numeral 21 indicates the transmitter or source of ultrasonic energy. A computer-adjustable electronic oscillator 101 is designed to operate at the frequency of the ultrasonic energy to be used, which is ordinarily between approximately 2 to 10 Mhz. The output of the oscillator connects by means of a lead 102 to a gate 103. The output of gate 103 connects through a lead 104 to the transmitting trandsucer 21. The first and last of the plurality of receiving transducers are shown in FIG. 9, and indicated by reference numerals 22a . . . 23n, it being understood that any number of such sensors may be provided, but are not shown for purposes of clarity. In FIG. 9, a number of parallel data channels, one for each sensor, are provided, and again, only the first and last are shown. The following description is set forth in terms of the data channel including receiver 22a, but it will be understood that the description applies to any of the data channels.

Receiver 22a is connected to the input of an amplifier 105. This amplifier serves to boost the received signals to a workable voltage level for the other blocks in the channel, and should preferably be of a low input noise design, for obvious reasons. The output of amplifier 105 connects via a lead 106 to the input of a time-of-flight detector 110. The output of time-of-flight detector 110 connects by means of a lead 111 to an analog to digital converter 112. The output of converter 112 connects in turn by means of a lead 113 to a storage register 114. Register 114 connects by a lead, or a set of leads for parallel data indicated by reference numeral 115, to the digital computer 116. Elements 105n through 115n are provided for the data channel which includes receiver 22n, and these elements are identical to elements 105-115 for the data channel described above.

The timing and control circuits 117 may be part of computer 116, or may be separate therefrom. Timing and control 117 is used to control and synchronize the system by means of a plurality of timing and control lines, generally designated by reference numeral 118, which connect to register 114, converter 112, detector 110, gate 103, and oscillator 101.

In operation, the computer and control circuits adjust the frequency of oscillator 101 as desired for a particular scan. The timing and control circuits enable gate 103 for a short interval thereby causing transmitter trandsucer 21 to emit a burst, short pulse, or coded pulse of ultransonic energy. Energy received by receiving transducer 22a is amplified by amplifier 105 and applied to time-of-flight detector 110. Device 110 serves both to detect the first significant excursion of the receiver output signal above the noise level, and detects the pulse arrivals to provide an output signal indicative of the elapsed time from transmit to receive. This can be done either by detecting the first significant excursion of the signal above the noise level, or by measuring group velocity. The time signal on lead 111 is digitized and stored in register 114. Similar measurements are made with the remaining receiver transducers, with the result that all registers 114–114n are filled with data. On command signal, these data are read into the computer for later use in reconstruction. Meanwhile, in case of the type of sensor shown in FIG. 4, the array can be angularly repositioned for the next data point. It will be appreciated with the closed boundary types of sensors shown in FIGS. 5, 7 and 8, only about a 1 millisecond delay is required between pulses, to allow unwanted echoes to damp out. It will further be appreciated that in case of a closed boundary-type transducer array the switching and control 57 would be interposed in leads 104 and 106, under control of the computer, to selectively connect given transducers to the oscillator and gate.

Although the block diagram of FIG. 9 shows parallel data channels, it would also be possible to use a serial technique of data acquisition, with the addition of suitable multiplexing switching networks, as are generally known in the prior art. A combination serial-parallel method may also be used, with successive groups of receivers being connected to a limited number of parallel channels by multiplexing techniques. This technique would have the advantage of moderately fast measurements while providing some economy of circuitry. Of course in the case of a scanning technique such as indicated in the diagram of FIG. 1, a serial technique would be required, with successive data points being measured and collected under computer control.

After all time-of-flight data have been measured, and shifted into computer 116, a suitable reconstruction technique may be used as previously discussed to compute the acoustic velocity at each picture element within the plane of the body being scanned.

These values can be displayed by any suitable graphic device, for example a CRT 120, by reading out the calculated values from computer 116 to a digital to analog converter 121, having an output connecting to an input 122 of the CRT. Techniques for generating CRT images from computer stored data are generally known in the art, and will not be discussed in detail here.

As indicated in FIG. 9, an amplitude detector 130 can optionally be included in each data channel. Amplitude detector 130 measures the strength of each transmitted pulse (after fixed gain amplification by amplifier 105). The output of amplitude detector 130 is applied to A to D converter 112 by a lead 131 for conversion to digital form. The digitized amplitude is then applied via a lead 132 to register 114, which would be designed to accommodate both time-of-flight and amplitude data. Elements 130n through 132n are provided for the other data channels and are identical to elements 130 through 132. Computer 116 would then reconstruct both velocity data at each picture element as previously described, and also attenuation coefficient data at each picture element.

Acoustic determination of the spatial distribution of acoustic attenuation coefficients have of course been done in the prior art, subject to the difficulties described in the *Background of the Invention* section above. However, it has been found that the attenuation data even when not corrected for reflection and refraction, when used in conjunction with the velocity data provided by the present invention, can lead to a synergistic effect so as to provide the diagnostician with a much greater source of information. To this end, comparisons can be made on the acoustic velocity data for a given point and the attenuation coefficient for the same point, as compared with tables of values for different types of normal and abnormal tissues, as previously experimentally determined. These values may in many cases definitely indicate the type of tissue present, or in other cases may raise a likelihood of the existence of abnormal tissues, so as to indicate the need for other diagnostic techniques.

The data for attenuation can be combined in an image form with the velocity data by means of a color CRT display. In that case, assume that CRT 120 is a color display, with the velocity data applied to input 122 which energizes one color of the display. The attenuation data is fed from the computer to another digital to analog converter 123, and then to an input 124 of the color CRT, which excites another color. Both velocity and attenuation information are then mapped into a color display of the characteristics of the tissue.

Additional scans can be made using different frequencies of ultrasonic energy, by reprogramming adjustable frequency oscillator 101. Reconstructions can then be made either of velocity or attenuation data at any number of different frequencies. The provision of an additional D to A converter 125 connected from the output of the computer and to an input 126 for the third color of the color CRT permits display of additional information on the CRT. Since both acoustic velocity and attenuation may in general vary as a function of frequency, a three-color display will permit display of superimposed velocity data, attenuation data, or any combination thereof, at different frequencies.

The effect of refraction on the assumption that the ray paths through the body are straight lines joining the transducers seems minimal, at least for reconstructions of a moderate number of picture elements. However, it is clear that high resolution images of acoustic refractive indices, or of attenuation coefficients, within heterogeneous tissues will require ray path corrections to be incorporated into the reconstruction process. The first reconstruction of index of refraction obtained by assuming straight ray paths may be used in subsequent reconstructions calculated along curved paths. It is thought that the first reconstruction is close enough to the final answer to allow an iterative solution to be implemented in which refractive indices calculated from a reconstruction are used to calculate the ray paths to be used in the succeeding reconstruction. Such as iterative process, if it converges, should allow higher resolution images to be obtained.

The refractive index information obtained by the present invention can be used to improve the accuracy and resolution of the prior art acoustic measurement and imaging systems discussed earlier in the background of the invention, by permitting calculation along the actual curved paths of the beams. For example, the information provided by the present invention can be used to correct for aberrations in synthetic focus B-scan imaging. Such images have been previously made on the assumption of straight ray paths through the object. See S. A. Johnson, et. al, "Digital Computer Simulation Study of a Real-Time Collection, Post-Processing Synthetic Focusing Ultrasound Cardiac Camera," *Acoustical Holography and Imaging, Vol. 6*, Plenum Press, New York, (1975). Once the distribution of index of refraction in the object space is determined according to the present invention, the correct ray path may be traced and the corresponding acoustic path length in the B-scan can be more accurately determined.

According to the present invention, we have thus provided a method of, and apparatus for, examining the internal structure of a body by measuring the time-of-flight of acoustic energy through the body, and reconstructing the spatial distribution of velocities, or refractive indices, within the body. The information thus obtained provides a quantitative measure of an intrinsic property of the material or materials within the body, and it also provides data for producing imagery of the internal structure. The velocity data can be combined in useful ways with attenuation data to provide an even greater wealth of information on the internal structure of the body.

We claim:

1. A method of examining the internal structure of a body comprising the steps of:
   (a) transmitting acoustic energy through said body from a plurality of different directions;
   (b) measuring the time-of-flight of the acoustic energy through the body; and
   (c) mathematically reconstructing the acoustic velocity at a plurality of points within said body.

2. A method according to claim 1 including the further step of displaying the acoustic velocity values to form a map or image of the internal structure of the body.

3. The method of measuring the spatial distribution of acoustic velocities within a plane of interest through a body, comprising the steps of:
   (a) transmitting pulses of acoustic energy through said body from different directions along a plurality of paths lying substantially in said plane;
   (b) receiving the acoustic energy pulses thus transmitted through the body;
   (c) measuring the time-of-flight of said pulses; and
   (d) mathematically reconstructing the acoustic velocity at a plurality of points within the plane of interest in the body.

4. A method according to claim 3 wherein said steps of transmitting and receiving comprise scanning a transmitter and receiver along opposite sides of the body within the plane of interest, for a plurality of angular relationships between the body, and the transmitter and receiver.

5. A method according to claim 3 wherein said step of transmitting comprises propogating a fan-shaped beam of acoustic energy through said body.

6. A method according to claim 3 wherein said step of transmitting comprises propogating the cylindrical beam of acoustic energy through said body.

7. A method of characterizing the material within a body by measuring acoustic velocities and attenuation coefficients within the body, comprising the steps of:
   (a) transmitting pulses of acoustic energy from a plurality of different directions through the body substantially along a plane of interest;
   (b) receiving the acoustic energy thus transmitted through the body;
   (c) measuring the time of flight of said pulses;
   (d) measuring the amplitude of the received pulses;
   (e) reconstructing the distribution of acoustic velocities at a plurality of points within the plane of interest; and
   (f) reconstructing the attenuation coefficients at a plurality of points within said plane of interest.

8. A method according to claim 7 including the further step of comparing the acoustic velocity values and attenuation coefficient values against known values, whereby to identify the material at said points within the said body.

9. A method of imaging the internal structure of a body along a plane of interest therethrough, comprising the steps of:
   (a) scanning the body through the plane of interest by transmitting ultrasonic pulses through the body from a plurality of different directions along the plane, and receiving the pulses thus transmitted through the body;
   (b) measuring the time-of-flight of said pulses from transmission to reception;
   (c) mathematically reconstructing the acoustic velocity at a plurality of picture elements through the plane of interest; and
   (d) visually displaying the velocity data to form a sectional image of the body along said plane.

10. A method according to claim 9 wherein said step of displaying comprises displaying said velocity data on a cathode ray tube display.

11. A method according to claim 9 further including the steps of performing additional scans, measurements, and reconstructions using a different frequency of ultrasonic energy to obtain an additional visual display for said different frequency of ultrasonic energy.

12. A method according to claim 11 wherein said step of displaying comprises displaying the different sets of velocity data for different frequencies as different colors on a color cathode ray tube display.

13. A method according to claim 9 further including the steps of:
   (a) measuring the amplitude of the received pulses;
   (b) mathematically reconstructing the attenuation coefficients at said plurality of picture elements throughout said plane; and
   (c) displaying said attenuation coefficient data in conjunction with said velocity data.

14. A method according to claim 13 wherein said display comprises displaying said velocity data and said attenuation coefficient data as different colors on a color cathode ray tube display.

15. Apparatus for examining the internal structure of a body comprising:

(a) means for transmitting acoustic energy through said body from a plurality of different directions;
(b) means for measuring the time-of-flight of the acoustic energy through the body; and
(c) means for mathematically reconstructing the acoustic velocity at a plurality of points within said body.

16. Apparatus according to claim 15 further including means for displaying the acoustic velocity values to form a map or image of the internal structure of the body.

17. Apparatus for measuring the spatial distribution of acoustic velocities within a plane of interest through a body, comprising:
(a) means for transmitting pulses of acoustic energy through said body from different directions along a plurality of paths lying substantially in said plane;
(b) means positioned in relation to said transmitting means for receiving acoustic energy pulses transmitted through the body;
(c) measurement means operatively connected to said receiving means, for producing signals indicative of the time-of-flight of said acoustic energy pulses; and
(d) calculator means connected to receive said signals, for reconstructing the acoustic velocity at a plurality of points within the plane of interest in the body.

18. Apparatus according to claim 17 including means for positioning and scanning said transmitting means and receiving means along opposite sides of a body within the plane of interest, and means for adjusting the angular relationship between the body, and the transmitter and receiver between successive scans.

19. Apparatus according to claim 17, wherein said transmitting means comprises an ultrasonic transducer adapted for propogating a fan-shaped beam of acoustic energy.

20. Apparatus according to claim 17, wherein said transmitting means comprises an ultrasonic transducer adapted for propogating a cylindrical beam of acoustic energy.

21. Apparatus according to claim 17 further including amplitude measurement means operatively connected to said receiving means, for producing amplitude signals indicative of the amplitude of the received acoustic energy pulses and wherein said calculator means is further connected to receive said amplitude signals for reconstructing the acoustic attenuation coefficient at a plurality of points within a plane of interest in the body.

22. Apparatus according to claim 17 further including means for adjusting the frequency of said acoustic energy pulse transmitting means, whereby acoustic velocity reconstruction may be obtained for different frequencies.

23. Apparatus according to claim 22 further including a color cathode ray tube display connected to said calculator means, for displaying the acoustic velocities at the plurality of points within the plane of interest within the body in different colors for different frequencies of acoustic energy.

24. Apparatus according to claim 21, further including color cathode ray tube display means connected to said calculator means, for displaying acoustic velocity and acoustic attenuation coefficient data within the plane of interest of the body in different colors.

25. Apparatus for examining the internal structure of a body along a plane of interest therethrough, comprising:
(a) an ultrasonic source adapted upon energization for emitting ultrasonic energy;
(b) means for receiving ultrasonic energy;
(c) mounting means for positioning said source and said receiving means on opposite sides of a zone for accommodating a body to be examined;
(d) means connected to said mounting means for angular adjustment thereof;
(e) detector means connected to said receiver means, for producing time-of-flight measurement signals for received pulses;
(f) control means operatively connected for repetitively energizing said source and for time referencing said detector for successive time-of-flight measurements, and operatively connected to said angular adjustment means for angularly repositioning said mounting means between successive time-of-flight measurements; and
(g) computation means connected to said detector to receive said time-of-flight signals, for mathematically reconstructing the spatial distribution of acoustic velocities at a plurality of points within the plane of interest.

26. Apparatus according to claim 25 wherein said means for receiving said ultrasonic energy comprises an array of ultrasonic transducers, and wherein said detector means comprises plural detector channels.

27. Apparatus according to claim 25 further including positional adjustment means for adjusting the position of said source and receiving means to different planes along the body.

28. Apparatus according to claim 25 including display means connected to said computation means, for visually displaying said spatial distribution of acoustic velocities.

29. Apparatus for examining the internal structure of a body along a plane of interest therethrough, comprising:
(a) means defining a closed boundary array of ultrasonic transducers having an aperture for receiving a body to be examined;
(b) an ultrasonic frequency generator for selective excitation of said transducers;
(c) detection means for measurement of time-of-flight of received pulses;
(d) switching means for selectively connecting individual transducers of said array to said generator and other transducers to said detection means, so as to provide transmission of energy pulses through the body;
(e) control means connected to said switching means for stepping through a sequence of different transducer connections to obtain a plurality of time-of-flight measurements; and
(f) computation means connected to said detection means to receive said time-of-flight measurements, and operable to mathematically reconstruct the spatial distribution of acoustic velocities at a plurality of points within the plane of interest.

30. Apparatus according to claim 29 further including a cathode ray tube display connected to said computation means, for displaying a map or image of the acoustic velocity distribution across the plane of interest.

* * * * *